(12) United States Patent
König et al.

(10) Patent No.: US 6,451,606 B1
(45) Date of Patent: Sep. 17, 2002

(54) RECEPTACLE UNIT FOR SOLUTIONS, IN PARTICULAR SOLUTIONS FOR CALIBRATION OF SENSORS FOR MEASURING PHYSIOLOGICALLY RELEVANT PARAMETERS

(75) Inventors: Christoph König, Wiesbaden-Auringen; Gerhard Mager, Bad Homburg; Petra Abel, Friedberg, all of (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/495,392

(22) Filed: Jan. 31, 2000

(30) Foreign Application Priority Data

Jan. 30, 1999 (DE) .......................... 199 03 704

(51) Int. Cl.$^7$ .............................................. G01N 31/00
(52) U.S. Cl. ............................ 436/8; 436/180; 422/61; 422/82.01; 422/99; 422/100; 73/1.01; 73/1.02; 73/1.03; 204/409
(58) Field of Search ....................... 436/8, 180; 422/61, 422/68.1, 82.01, 99, 100, 102; 73/1.01, 1.02, 1.03; 324/438, 439; 204/416, 418, 419, 400, 401, 409

(56) References Cited

U.S. PATENT DOCUMENTS

| | | | | |
|---|---|---|---|---|
| RE29,725 E | * | 8/1978 | Johnson et al. ............... 435/12 |
| 4,654,127 A | * | 3/1987 | Baker et al. ................ 205/792 |
| 4,871,439 A | | 10/1989 | Enzer et al. ................ 204/401 |
| 4,965,047 A | * | 10/1990 | Hammond ................... 422/58 |
| 4,978,502 A | * | 12/1990 | Dole et al. .................... 422/58 |
| 5,096,669 A | | 3/1992 | Lauks et al. .................. 422/61 |
| 5,145,565 A | * | 9/1992 | Kater et al. ................. 205/792 |
| 5,284,570 A | | 2/1994 | Savage et al. .............. 204/422 |
| 5,290,518 A | * | 3/1994 | Johnson ....................... 422/58 |
| 5,393,391 A | * | 2/1995 | Dietze et al. ............ 205/781.5 |
| 5,421,981 A | | 6/1995 | Leader et al. ............... 204/409 |
| 5,489,414 A | * | 2/1996 | Schreiber et al. ............. 422/64 |
| 5,804,141 A | * | 9/1998 | Chianese ..................... 422/63 |
| 5,885,533 A | * | 3/1999 | Savage et al. .............. 422/102 |
| 5,968,329 A | * | 10/1999 | Anderson et al. ........... 204/402 |

FOREIGN PATENT DOCUMENTS

| | | |
|---|---|---|
| DE | 33 12 923 | 10/1984 |
| DE | 295 11 566 | 1/1996 |
| DE | 197 02 362 | 1/1998 |
| EP | 354895 | 2/1990 |
| WO | WO 85/04719 | 10/1985 |
| WO | WO 86/05590 | 9/1986 |

\* cited by examiner

*Primary Examiner*—Maureen M. Wallenhorst
(74) *Attorney, Agent, or Firm*—Kenyon & Kenyon

(57) ABSTRACT

A disposable receptacle unit for solutions is described, in particular for solutions used in calibrating sensors for measurement of physiologically relevant parameters. The receptacle is a disposable blister pack for a single use that includes several chambers to hold solutions. Each chamber is connected to a sample channel by an outlet channel sealed by a sealing element. The sensors for measurement of physiological parameters are preferably part of the receptacle unit. To calibrate the sensors, the calibration solutions in the chambers are metered into the sample channel after opening the corresponding sealing elements. After the treatment, the receptacle unit is discarded together with the sensors.

14 Claims, 3 Drawing Sheets

RECEPTACLE UNIT FOR SOLUTIONS, IN PARTICULAR SOLUTIONS FOR CALIBRATION OF SENSORS FOR MEASURING PHYSIOLOGICALLY RELEVANT PARAMETERS

The present invention concerns a receptacle unit for solutions, in particular solutions for calibration of sensors for measuring physiologically relevant parameters. In particular, the receptacle unit is a disposable module intended for a single use.

SUMMARY OF RELATED ART

Sensors are used in medical technology for measuring physiologically relevant parameters, such as urea during a dialysis treatment. These sensors must be calibrated because their operating parameters are subject to unpredictable variation due to both production differences and time spent in storage.

For calibration, small volumes of calibration solutions must be supplied to the sensors for measurement of physiologically relevant parameters. The calibration solution can be applied by manual or mechanical methods.

German Patent Application No. 33 12 923 A1 describes a receptacle unit for electrochemical analysis of electrolytic components of a fluid, in particular blood or urine, which has an electrode arrangement and a sample chamber to accommodate the fluid. The sample chamber is filled by the manufacturer with a standard electrolyte solution, which serves to precondition the electrode arrangement. After being emptied, the sample chamber is filled with the fluid to be analyzed. To perform the analysis, the receptacle unit is then placed in an analyzer.

European Patent No. 354,895 B1 describes a disposable measurement element consisting of a sensor part and a sampling part inserted into an analyzer. The sensor part has a measurement channel equipped with sensors and filled by the manufacturer with a calibration solution. When the disposable measurement element is inserted into the analyzer, the calibration solution is removed from the measurement channel of the sensor part, and the fluid to be analyzed is drawn from the sampling part into the measurement channel.

International Patent WO 86/05590 describes a disposable receptacle unit for analysis of blood samples, having a measurement channel filled with calibration solution by the manufacturer.

International Patent WO 85/04719 discloses an insertion card having a sample channel equipped with sensors for an analyzer. The card has a socket in which a cylinder with two chambers is mounted rotatably. One chamber is filled with a calibration solution by the manufacturer, while the other chamber holds the fluid to be analyzed. The cylinder may be rotated between two positions, where the chamber filled with calibration solution is connected to the sample channel in one position, and in the other position the chamber for holding the fluid to be analyzed is connected to the sample channel.

U.S. Pat. No. 5,096,669 A describes an insertion card for an analyzer where the calibration solution for the sensor is packaged in a small film bag. The bag is located in a well and is punctured by a mandrel, so that the calibration solution flows to the sensors by passing through channels provided in the insertion card.

Several sensors are required to measure the relevant physiological parameters during a dialysis treatment. Thus, several calibration solutions must be made available for calibration of these sensors.

An application system with several chambers to accommodate medicines is known from German Patent Application No. 197 02 362 A1. The application system has a dish-shaped container with an inlet connection and an outlet connection for an infusion solution. The container holds a metering insert having cylindrical chambers that are sealed tightly with a sealing film. After puncturing the sealing film, the chambers can be emptied into a gap space through which the infusion solution flows. The relatively expensive production costs of this system has proven to be a disadvantage.

U.S. Pat. No. 4,871,439 A describes a disposable unit with a sample channel on which are arranged several sensors for determining characteristic properties of a fluid. The disposable unit includes two chambers for holding calibration solutions for the sensors. The chambers holding the calibration solutions consist of aluminum foil heat-sealed at the edges. Releasing the contents of these chambers into the disposable unit is a relatively complicated operation.

A unit for testing biological fluids in which welded PE film is used as the supply bag for the system solution and for waste is described in German Utility Model No. 295 11 566 U1.

U.S. Pat. No. 5,284,570 A discloses an analyzer unit that includes a syringe.

An analyzer unit with a calibration solution container sealed by a puncturable membrane is described in U.S. Pat. No. 5,421,981 A.

SUMMARY OF THE INVENTION

The present invention is a disposable receptacle unit intended for a single use, with which several solutions can be made available. In particular, solutions for calibration of sensors for measuring physiologically relevant parameters easily under sterile conditions can be provided. The receptacle unit can be manufactured in large numbers at a relatively low cost.

Accordingly, in one aspect the invention is a receptacle for solutions used to calibrate sensors for measurement of physiologically relevant parameters, comprising a plate-like base body, an envelope of flexible material attached to one surface of the base body, and a plurality of chambers for holding the solutions, the chambers being formed between the base body and the envelope. The receptacle also can include an outlet orifice formed in each one of the plurality of chambers, a sealing element for sealing the outlet orifice, and sample channels connected to the outlet orifice of each chamber, adapted for receiving the solutions after the sealing elements are opened.

In another aspect, the invention is a method for calibrating sensors for measurement of physiologically relevant parameters, comprising the steps of inserting a receptacle having a plurality of chambers containing a metered amount of calibrating solutions in an analyzer, puncturing a sealing element of a selected one of the chambers with a ram portion of the analyzer, flowing the solution in the selected chamber into a central sample channel of the receptacle, connected to sensors, and reporting values measured by the sensors to the analyzer through electrical connections formed in the receptacle.

The receptacle unit can be, for example, a blister pack that can be produced inexpensively as a disposable article in large numbers. The receptacle unit has a base body, with the chambers being bordered by an envelope of flexible material forming sealed cavities together with the base body. No additional measuring and metering device is necessary, because the chambers for holding the solutions have a defined volume.

The blister pack receptacle unit preferably has a flat design and can be handled easily as a replaceable module. The base body of the receptacle unit may accommodate a plurality of chambers in a very small space. There is little or no possibility of the solutions becoming contaminated in the receptacle unit. Furthermore, little or no impurities from the environment can be entrained into the receptacle unit when the individual chambers are emptied.

To achieve a high packing density, the chambers are preferably arranged in a row, side by side. Several rows of chambers may also be provided. In this case, each row can have a connecting channel connecting the outlet channel of each chamber of that row with the sample channel.

The receptacle unit according to the present invention is particularly well suited for packaging portions of several solutions for calibration of sensors that measure physiologically relevant parameters. However, the unit may also be used to hold, for example, control solutions, conditioning solutions, cleaning solutions and disinfectant solutions.

The receptacle unit according to this invention allows reliable handling of small quantities of fluid. The solutions are made available packaged in individual portions and can be metered into the sample channel one after the other. If necessary, the order in which the solutions are metered into the sample channel can be preset through a suitable arrangement of chambers in the receptacle unit.

In a preferred embodiment of the receptacle unit which is used for calibration of sensors for measurement of physiologically relevant parameters, the sensors to be calibrated can be part of the receptacle unit. The receptacle unit can have a connection for supplying a sample to be analyzed into the sample channel, and a connection for removing the sample from the sample channel. For calibration of the sensors, the calibration solutions are metered from the chambers into the sample channel.

The arrangement of sensors on the receptacle unit has the advantage that it is not necessary to clean, disinfect or sterilize them. After a single use, the sensors can be discarded together with the receptacle unit. This is especially advantageous since electrochemical sensors react to many cleaning agents and disinfectants, potentially resulting in a considerable impairment, or even total loss, of function. Moreover, cleaning, disinfection or sterilization of sensors would be very labor-intensive in practical use and thus would not be practically feasible. This problem is solved with simple means and with great reliability by the disposable receptacle unit with sensors intended for a single use.

To establish an electrical connection between the sensors and the analyzer into which the module can be inserted, the receptacle unit advantageously can be provided with contacts to which the sensors are connected.

The chambers for holding the solutions may vary in design. However, it is especially advantageous if the chambers are designed so that they can be emptied by operating elements that act on the chambers from the outside. Such operating elements may be part of the analyzer.

In a preferred embodiment of this invention, a connecting channel running below the chambers on the back of the base plate is provided for connecting the outlet orifices of the chambers to the sample channel. The outlet orifices in this design can be holes in the base plate.

The connecting channel and sample channel can be expediently formed by grooves on the back of the base plate, covered by a film applied to the back of the base plate.

Additional holes sealed by the cover film on the back of the base body may also be provided in the base body beneath the chambers. These holes serve to fill the chambers with the solutions before applying the film to the back of the base body.

Manufacture of the receptacle unit can be further simplified by sealing the outlet orifice of the chamber with a part connected to the base body by a predetermined breaking zone. Thus, the base body can be manufactured together with the closing elements as an injection molded part. However, the closing element which seals the outlet channel of each chamber may also be a foil or film applied to the top of the base body to seal the outlet channel. A film applied to the back of the base body may also be provided for sealing the connecting hole.

To produce the flow connection between the chambers and the sample channel, the sealing film can be advantageously punctured with a ram provided in each chamber. The chambers are preferably designed so that the rams for puncturing the sealing film are secured in the chambers.

BRIEF DESCRIPTION OF THE DRAWINGS

One embodiment of this invention is explained in greater detail below with reference to the drawings.

DETAILED DESCRIPTION OF THE EMBODIMENTS OF THE INVENTION

Figure 1:
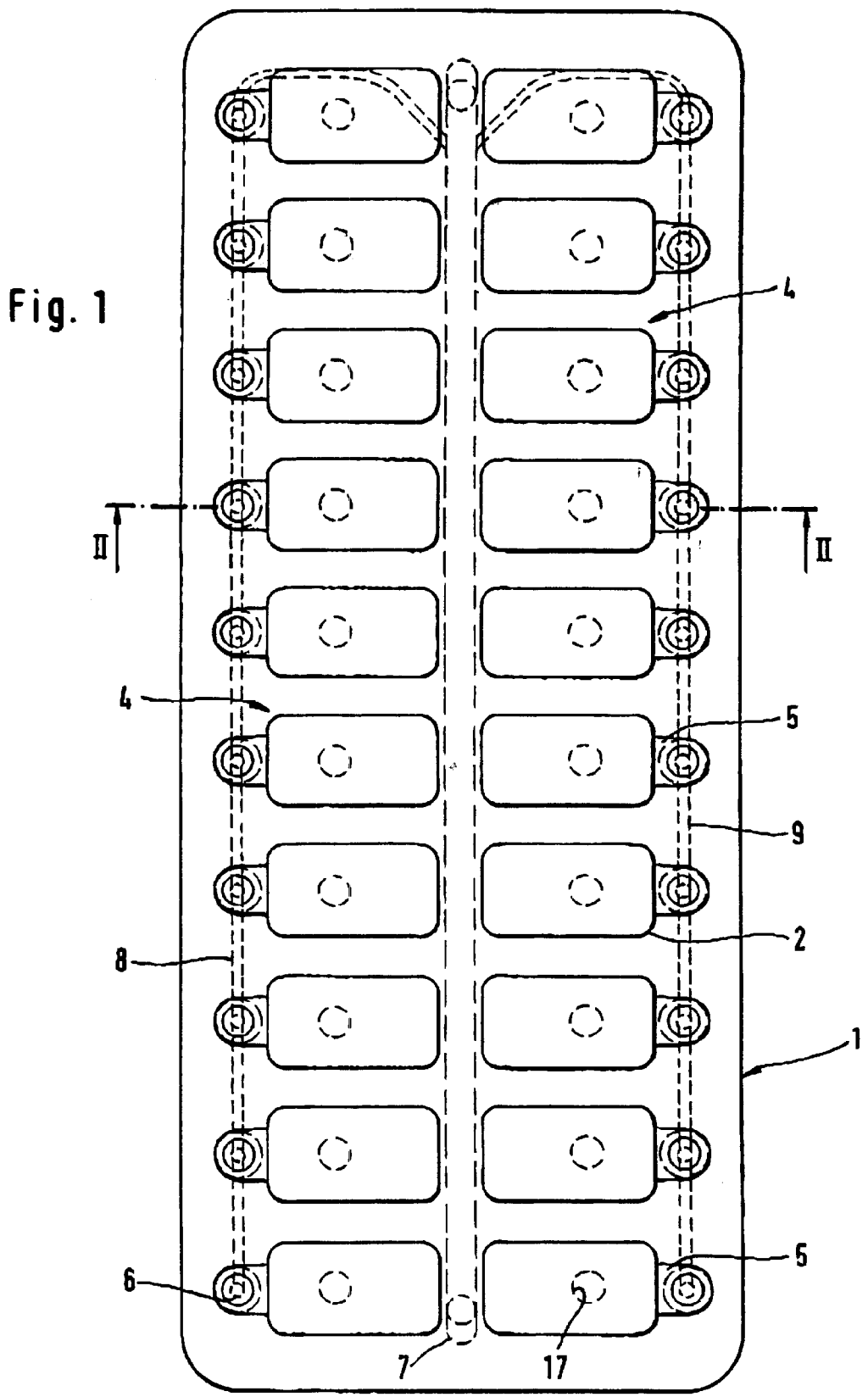
FIG. 1 is a top view of a first embodiment of a receptacle unit for calibration solutions.
Figure 2:
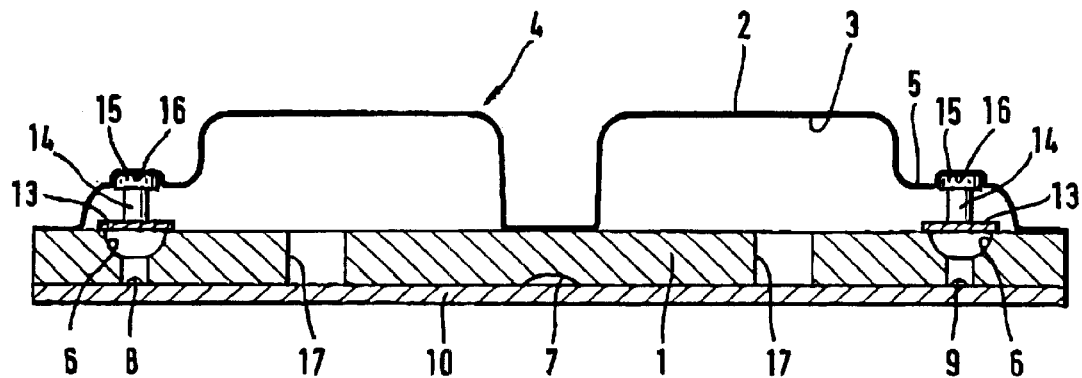
FIG. 2 is a cross sectional view through the receptacle unit shown in FIG. 1 along line II—II.
Figure 3:
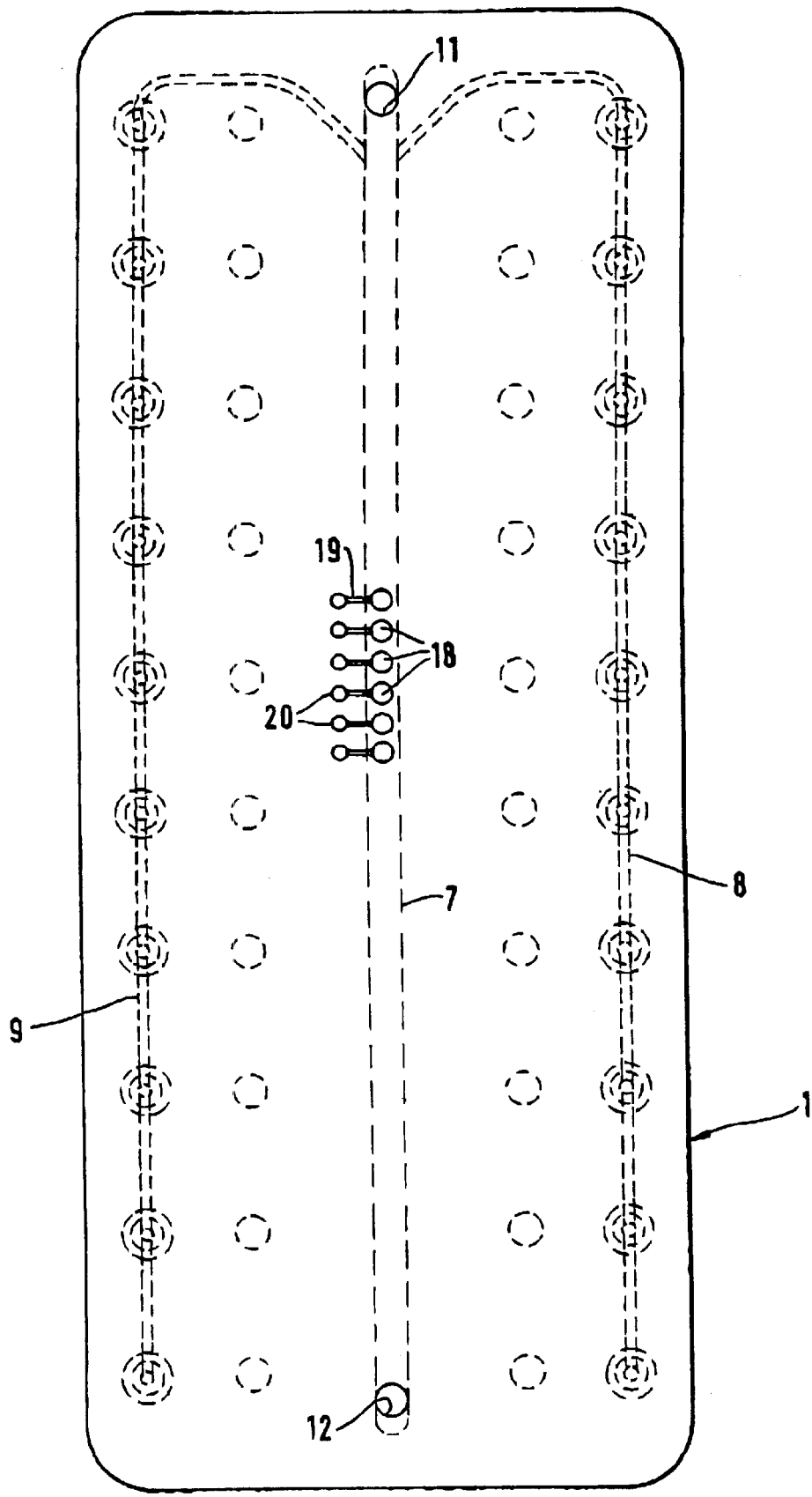
FIG. 3 is a bottom view of the receptacle unit shown in FIG. 1.

FIGS. 1 through 3 show a receptacle unit that includes a blister pack used to hold the solutions for calibration of electrochemical sensors for measurement of physiologically relevant parameters. For example, the sensors can be used for measuring urea during a dialysis treatment. The receptacle unit includes a rectangular plate 1, preferably made of a transparent plastic. A transparent plastic film 2 is shaped to form two rows side by side of ten recessed wells 3 each, and is applied to the top of the plastic plate. The plastic film 2, which is preferably welded or glued to the plate 1, forms a total of twenty chambers 4 together with the plate 1. Chambers 4 have an essentially rectangular base area. On the shorter side, chambers 4 have a projection 5 pointing outward and having a smaller height than the rest of the chamber.

Connecting holes 6 preferably are provided in the plastic plate 1 in the area of the flat projections 5 of the chambers. The back surface of the plate 1 has a central groove 7 extending in the longitudinal direction between the chambers 4, and two side grooves 8, 9 parallel to the lines of the connecting holes 6, beneath the flat projections 5 of chambers 4. The side grooves 8, 9 open into the central groove 7 on a narrow side of the plastic plate.

A cover film 10 can be glued or welded to the back of plastic plate 1, so that two side connecting channels 8, 9 and one central sample channel 7 are formed. At one end of sample channel 7, the cover film 10 has a connection 11 for supplying a sample to be analyzed, and at the other end of the sample channel it has a connection 12 for removing the sample (FIG. 3).

The connecting holes 6 in the plastic plate 1 are sealed with sealing elements 13. The sealing elements can be circular film pieces which are applied to the top of the plastic plate 1 in the flat projections 5 of the chambers 4. Rams 14 are inserted into the flat projections 5 of the chambers 4 to open the sealing elements. The rams 14 have a round head 15, which sits in a corresponding recess 16 in the film. The rams are held with a slight clamping action between film 4 and plastic plate 1. The chambers of the receptacle unit can have a volume of approximately 1 ml and can be filled with different calibration solutions. To be able to fill the chambers, additional holes 17 are provided in the plastic plate 1 in the area of the chambers, for adding the reagents to the chambers before applying the cover film 10 to the back of the plate 1.

The ion-selective sensors 18 for measurement of physiological parameters of a fluid flowing through the sample channel 7 can be located on the back of plastic plate 1. The electrical contacts of the sensors are connected by connecting lines 19 to a row of contacts 20 on the back of the cover film 10.

During use, the replaceable module receptacle unit is inserted into an analyzer (not shown) having electronic measurement equipment to process the electric signals of the sensors. The analyzer has preferably hydraulic connectors for connections 11, 12 of the receptacle unit, for supplying and removing the sample, as well as electrical contacts to establish an electrical connection to the corresponding contacts 20 of the receptacle unit.

The sample to be measured is removed at the machine end, sent through the sample channel 7 past sensors 18 and then discarded. The sensors then deliver the measured values to the analyzer of the dialysis machine, where they are processed and/or displayed.

To calibrate the sensors 18, the calibration solutions in the individual chambers can be metered one after the other into the sample channel 7. To do so, the ram 14 in the flat projection 5 of the chamber 4 to be emptied is pressed into the sealing film 13, thus puncturing it. The solution can then flow out of the chamber and into the central sample channel 7 through side connecting channel 8 or 9.

To empty the chambers, the analyzer can have an operating device having plungers provided for the individual chambers and sealing elements. The electromagnetically or pneumatically operated plungers of the analyzer open the sealing elements and compress the chambers 4 to be emptied, thus releasing the flow into the side connecting channels 8, 9 so that the respective calibration solution enters the sample channel 7. Thus, a fresh, sterile calibration solution that is free of contamination is available for each calibration. At the end of the treatment, the receptacle unit which is designed as a disposable unit is then discarded.

Figure 4:
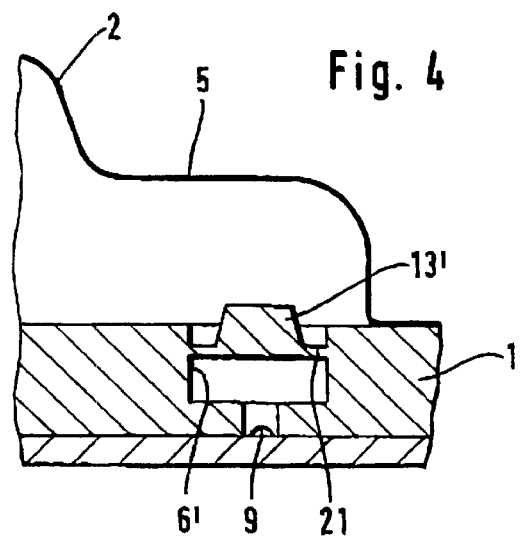
FIG. 4 is an enlarged partial view of another embodiment of the receptacle unit.

FIG. 4 shows a partial view of another embodiment of the receptacle unit. This embodiment differs from the embodiment described with reference to FIGS. 1–3 due to the sealing elements 13' with which the connecting holes 6' in the base plate 1 are sealed. The sealing elements 13' sit in the connecting holes 6' and are connected to the base body 1 by narrow webs 21. When the sealing elements 13' are pressed into the connecting holes 6', the narrow connecting web breaks, so that the calibration solution runs out of chamber 4 into the sample channel 7. The sealing elements 13' are punctured by the plungers of the operating device of the analyzer in which the receptacle unit is placed.

What is claimed is:

1. A receptacle for solutions used to calibrate sensors for measurement of physiologically relevant parameters, comprising:

a base body;
an envelope of flexible material attached to a front surface of the base body;
a plurality of chambers capable of holding a calibration solution, formed between the base body and the envelope;
an outlet orifice formed in each one of the plurality of chambers;
a sealing element for sealing the outlet orifice;
a sample channel in fluid communication with the outlet orifice of each chamber for receiving the calibration solutions after the sealing elements are opened;
sensors positioned in the sample channel which are calibrated upon contact with the calibration solutions; and
contacts on an external portion of the receptacle, the contacts for electrically connecting the sensors to an outside connection.

2. The receptacle according to claim 1, wherein the envelope is made of a plastic film.

3. The receptacle according to claim 1, further comprising a connecting channel formed on a back surface of the base body beneath the plurality of chambers, the connecting channel providing a conduit that connects the sample channel to the outlet orifice of each chamber.

4. The receptacle according to claim 3, wherein the connecting channel and the sample channel are defined by grooves formed on the back surface of the base body and by a film applied to said back surface of the base body.

5. The receptacle according to claim 4, wherein the base body includes a plurality of holes for filling the chambers that are sealed by the film applied on the back surface of the base body.

6. The receptacle according to claim 1, wherein the sealing element is connected to the base body by a breaking zone.

7. The receptacle according to claim 1, wherein the sealing element is one of a film and a foil for sealing the outlet orifice of each chamber.

8. The receptacle according to claim 7, further comprising a ram provided in each one of the plurality of chambers for puncturing the sealing element.

9. The receptacle according to claim 8, wherein the ram is secured within each chamber.

10. The receptacle according to claim 1, wherein the plurality of chambers includes chambers arranged in rows.

11. The receptacle according to claim 10, wherein the sample channel is connected to the chambers arranged in each of the rows, wherein the sample channel connects the outlet orifice of each chamber in a row.

12. The receptacle according to claim 1 further comprising a first connection in the base body for supplying into the sample channel a sample to be analyzed by the sensors, and a second connection in the base body for removing the sample from the sample channel, wherein the plurality of chambers contain the solutions for calibration of sensors, the sample provided from the solutions.

13. The receptacle according to claim 12, wherein the sensors in the sample channel to be calibrated form a unitary part with the receptacle.

14. A method for calibrating sensors for measurement of physiologically relevant parameters, comprising the steps of:

inserting a receptacle having a plurality of chambers containing a metered amount of calibrating solutions in an analyzer;
puncturing a sealing element of a selected one of the chambers with a ram portion of the analyzer;

flowing the solution in the selected chamber into a central sample channel of the receptacle;

measuring values of the solution with sensors located in the central sample channel; and reporting values measured by the sensors to the analyzer through electrical connections formed in the receptacle.

* * * * *